United States Patent
Roesler

(10) Patent No.: US 9,694,968 B2
(45) Date of Patent: Jul. 4, 2017

(54) INDIVIDUAL PACKAGING FOR ELONGATE OBJECTS

(71) Applicant: ROSE PLASTIC AG, Hergensweiler (DE)

(72) Inventor: Peter Roesler, Wangen (DE)

(73) Assignee: Rose Plastic AG (DE)

( * ) Notice: Subject to any disclaimer, the term of this patent is extended or adjusted under 35 U.S.C. 154(b) by 0 days.

(21) Appl. No.: 15/036,908

(22) PCT Filed: Nov. 21, 2014

(86) PCT No.: PCT/EP2014/003111
§ 371 (c)(1),
(2) Date: May 16, 2016

(87) PCT Pub. No.: WO2015/074761
PCT Pub. Date: May 28, 2015

(65) Prior Publication Data
US 2016/0272410 A1    Sep. 22, 2016

(30) Foreign Application Priority Data
Nov. 21, 2013  (DE) .......................... 10 2013 019 452

(51) Int. Cl.
*B65D 85/20*    (2006.01)
*A61B 17/86*    (2006.01)

(52) U.S. Cl.
CPC ............ *B65D 85/20* (2013.01); *A61B 17/865* (2013.01)

(58) Field of Classification Search
CPC ......... A61C 3/04; A61C 8/0048; A61C 8/008; A61C 8/0087; A61C 8/0089; A61B 17/865; A61B 50/20; A61B 50/30; A61B 2050/005; A61B 2050/0054; A61B 2050/0068; A61B 2050/0083; B25H 3/00; B65D 59/06; B65D 85/24; Y10S 220/918; Y10S 411/959

(Continued)

(56) References Cited

U.S. PATENT DOCUMENTS 2,746,506 A  *  5/1956  Ougljesa ................ F16B 39/24
                                                       411/134
2,877,681 A  *  3/1959  Brown ................... F16B 27/00
                                                       411/393

(Continued)

FOREIGN PATENT DOCUMENTS

DE          60015163        12/2005
DE        202007004638        6/2007

(Continued)

*Primary Examiner* — Chun Cheung
*Assistant Examiner* — Brijesh V. Patel
(74) *Attorney, Agent, or Firm* — Cohen & Brigsby, PC

(57) ABSTRACT

Packaging for elongate objects such as a screw (20, 30) having a head (21) of enlarged diameter and a bolt part (23, 24) having reduced diameter. The packaging (1) includes a packaging sleeve that is open at at least one end and that is made of an elastically bendable material. The packaging sleeve has at least one upper insertion opening (2) and securely holds the head (21) of the object screw (20) in an axial direction in an elastically expandable clamping collar (5) that is adjacent to the insertion opening (2) and maintains the bolt-side end of the object at a distance from the inside of the plastic packaging.

9 Claims, 4 Drawing Sheets

(58) Field of Classification Search
USPC ....... 206/63.5, 338–339, 364–366, 368, 446;
220/4.21–4.24, 4.27, 831, 844, 918;
604/192, 198, 403; D24/156; D3/203.1;
D9/432
See application file for complete search history.

(56) References Cited

U.S. PATENT DOCUMENTS

| | | | |
|---|---|---|---|
| 3,074,540 A | 1/1963 | Beich et al. | |
| 4,793,757 A * | 12/1988 | Peterson | F16B 43/00 411/353 |
| 4,925,030 A * | 5/1990 | Ball | A61M 37/0069 206/343 |
| 5,368,160 A * | 11/1994 | Leuschen | A61C 8/0087 206/339 |
| 5,437,368 A * | 8/1995 | Mikels | F16B 27/00 206/341 |
| 5,544,746 A * | 8/1996 | Dohi | F16B 27/00 206/346 |
| 5,582,299 A * | 12/1996 | Lazzara | A61C 8/0087 206/438 |
| 5,797,912 A * | 8/1998 | Runciman | A61B 17/8047 606/286 |
| 5,961,330 A * | 10/1999 | Hanson | A61C 8/0087 433/173 |
| 6,086,371 A * | 7/2000 | Bassett | A61C 8/0087 206/339 |
| 6,142,296 A * | 11/2000 | Klardie | A61C 8/0087 206/368 |
| 6,416,324 B1 * | 7/2002 | Day | A61C 8/008 433/173 |
| 8,083,054 B2 * | 12/2011 | Nihei | A61C 8/0087 206/368 |
| D659,829 S * | 5/2012 | Nihei | D24/156 |
| D731,169 S * | 6/2015 | Sakaguchi | D3/203.1 |
| 2002/0170840 A1 * | 11/2002 | Happonen | A61B 17/105 206/338 |
| 2005/0218024 A1 | 10/2005 | Lang et al. | |
| 2008/0230423 A1 * | 9/2008 | Loeffler | A61B 17/865 206/438 |

FOREIGN PATENT DOCUMENTS

| | | |
|---|---|---|
| DE | 202007004638 U1 | 6/2007 |
| DE | 202010007487 U1 | 9/2010 |
| WO | 9939655 A1 | 8/1999 |

* cited by examiner

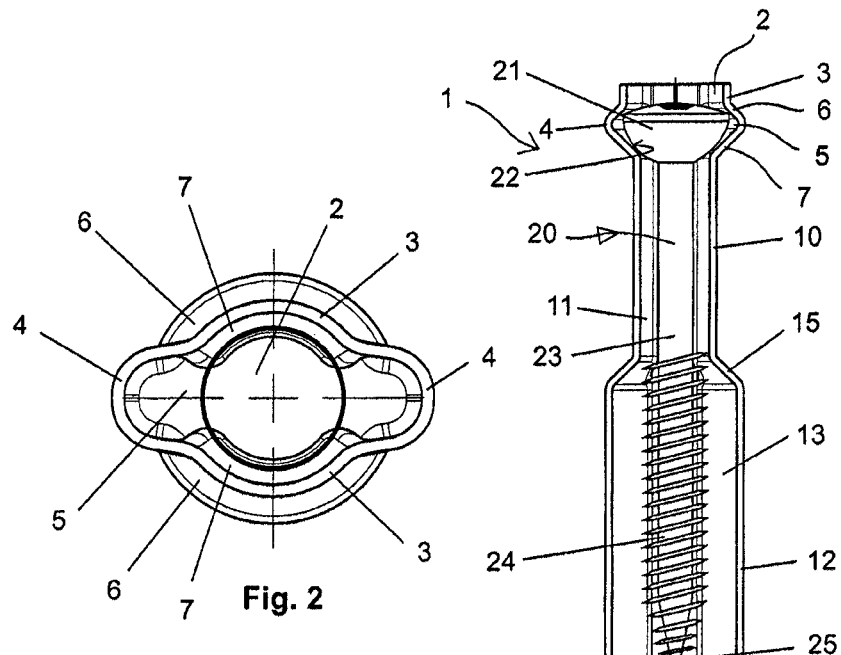
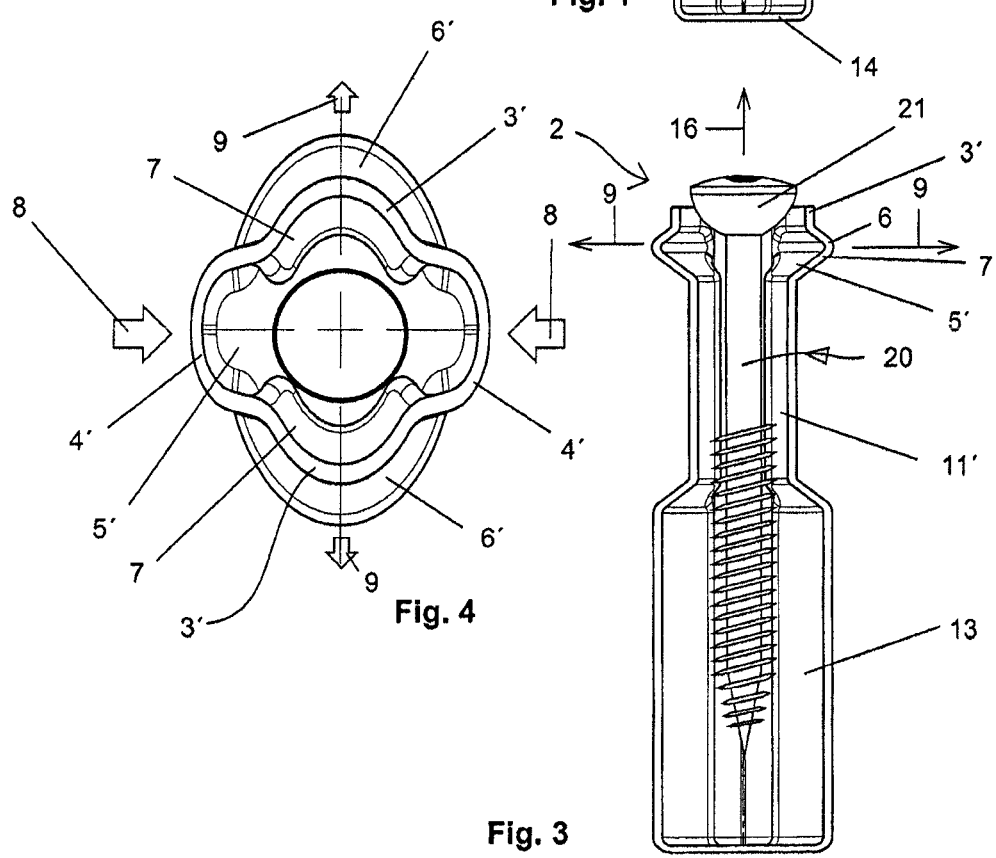

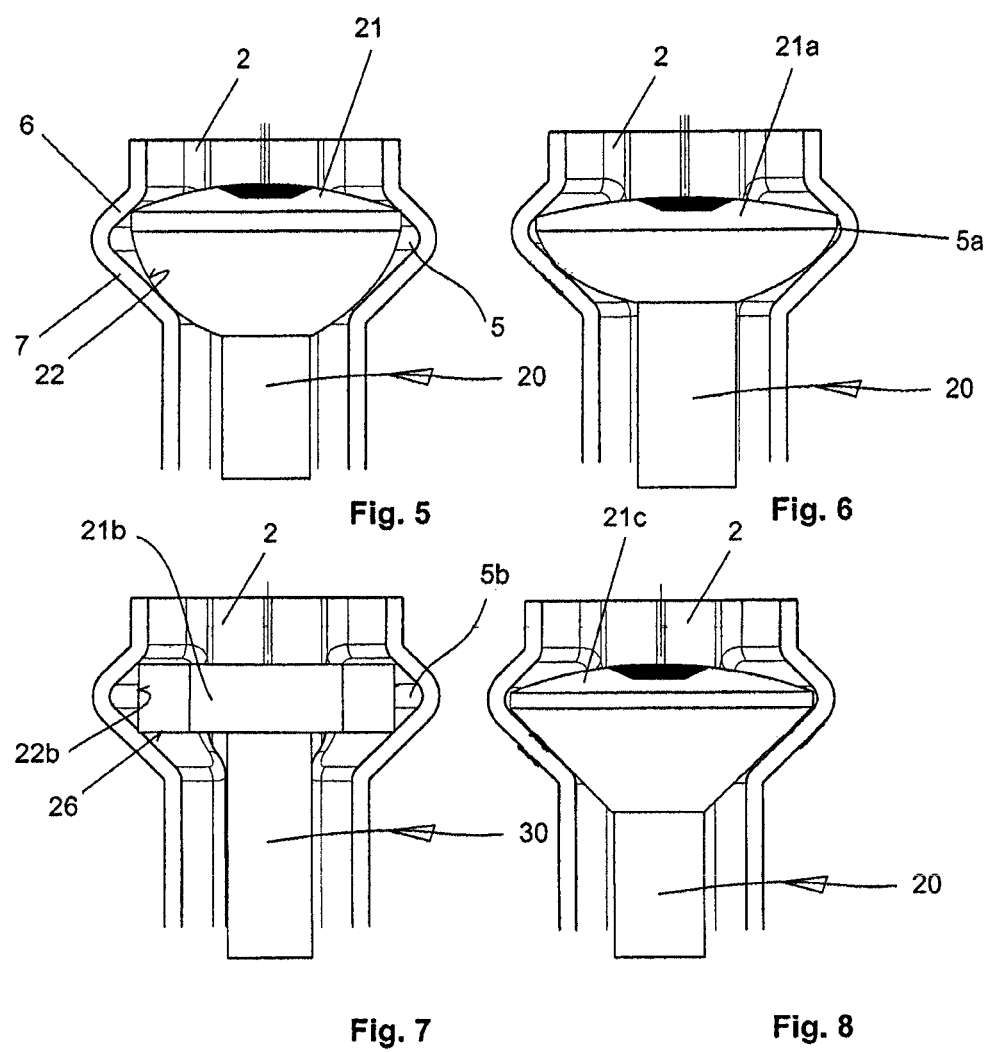

INDIVIDUAL PACKAGING FOR ELONGATE OBJECTS

BACKGROUND OF THE INVENTION

Field of the Invention

The invention relates to an individual packaging for elongated objects, which consist at least of a head having an increased diameter and a bolt part that follows it with a reduced diameter, such as, for example, bone nails, ejector pins, and the like, wherein the individual packaging consists of an approximately cylindrical packaging sleeve that is open at the face end at least on one side, composed of an elastically bendable material, which sleeve has at least one upper introduction opening for introduction of the elongated object.

Discussion of the Prior Art

Individual packagings of the type stated initially are used for packaging of sensitive objects, such as, for example, drills, ejector pins for plastic injection-molding molds, individual screws, and the like.

In this regard, the invention proceeds from the fact that the elongated object to be packaged has a head having an increased diameter. Such elongated objects are, for example, bone screws for use in surgery, or ejector pins for plastic injection-molding molds, and the like.

Particularly in the case of bone screws, which have a sharp-edged thread, the disadvantage existed until now that with the conventional plastic packaging, there was the risk that the sharp-edged thread of the bone screw would scrape off plastic particles on the inside of the plastic packaging, which were then carried into the thread channel of the bone screw. When the bone screw was screwed into human or animal bone substance, the particles were then carried into the bone substance and led to wound-healing problems.

In the case of precision-machined ejector pins for the tools of plastic injection-molding tools, for example, the disadvantage also existed that the bolt of the ejector pin, which had been machined to a precision of micrometers, would be damaged in spite of being packaged in a sleeve-like plastic packaging, because the sensitive bolt end could make direct contact with the inside of the plastic packaging.

SUMMARY OF THE INVENTION

The invention is therefore based on the task of further developing an individual packaging for elongated objects, of the type stated initially, in such a manner that damage to and/or contact of the bolt-side end of the object provided with a head, against the inside of the plastic packaging, is excluded.

The solution of the stated task is directed to individual packaging for elongated objects such as screw (20, 30), which consist at least of a head (21) having an increased diameter and a bolt part (23, 24) that follows it with a reduced diameter, such as, for example, bone nails, ejector pins, and the like, wherein the individual packaging (1) consists of an approximately cylindrical packaging sleeve that is open at the face end at least on one side, composed of an elastically bendable material, which sleeve has at least one upper introduction opening (2) for introduction of the elongated object such as screw (20, 30), characterized in that the individual packaging (1) merely holds the head (21) of the screw (20) to be held in a secure position, in an elastically expandable clamping collar (5) that follows the introduction opening (2) in the axial direction, and that the bolt-side end of the object is held at a distance from the inside of the plastic packaging, maintaining this distance.

It is an essential characteristic of the invention that the individual packaging merely holds the head of the object to be held in a secure position, in an elastically expandable clamping collar that follows the introduction opening in the axial direction, and that the bolt-side end of the object is held at a distance from the inside of the plastic packaging, maintaining this distance.

This results in the advantage that only the head of the object to be held is held in a clamping collar of the packaging, and all the other parts of the object no longer come into contact with the inside of the packaging. Instead, they are held at a distance from the inside of the packaging, maintaining this distance, because only the head of the object itself is accommodated in a type of clamping holder in a clamping collar of the individual packaging.

In order to ensure that the head of the object, which is accommodated in a clamping holder of the individual packaging, can also be removed from the packaging again, the invention provides that the clamping collar of the individual packaging is configured so that it can be elastically widened by finger pressure or mechanically, by means of a suitable automated packaging tool.

For this purpose, it is provided that the clamping collar does not lie against the head by 360° with reference to the circumference of the head of the object, but rather only by a circumference region of less than 340°, for example. The regions that do not form the clamping collar (here, in other words, the angle regions of twice 10 degrees, which lie opposite one another) are configured as widened regions of a ring collar that forms the clamping collar, which regions project beyond the outer circumference of the packaging. They follow the clamping collar directly, in one piece, and are composed of the same material. In this way, it becomes possible for the two radial widened regions, which preferably lie diametrically opposite one another, to be compressed with finger pressure or mechanically, so that in this way, the clamping collar is elastically widened and the clamping seat on the outer circumference of the head of the object is cancelled out.

The invention is not restricted to placement of two diametrically opposite widened regions that can be compressed inward, in the radial direction, by finger pressure or mechanically, in each instance. Three or more widened regions that can be compressed and lie opposite one another can also be provided.

It is preferred if these widened regions lie in the same horizontal plane. The invention is not restricted to this. They can also be disposed offset from one another in the axial direction, with reference to a horizontal plane.

It is preferred if the elastically deformable, compressible widened regions extend over the entire axial length of the packaging. This results in the advantage that when the widened regions are compressed, not only does the head region of the individual packaging, with the clamping collar disposed there, widen elastically, but furthermore, the sleeve part of the individual packaging, which follows the head region, does so as well.

However, the invention is not restricted to this. In another embodiment, it can be provided that the elastically deformable widened regions extend only by a specific axial length along the axial length of the individual packaging and are shorter than the length of the individual packaging.

It is furthermore important to the invention that a sleeve part follows the head part of the individual packaging, in which the clamping collar for the holder of the head of the object is disposed, which part has a wider diameter than the head part.

Therefore, the risk that the bolt part and/or thread part of the object makes contact with the inside of the sleeve part no longer exists, even in the event of severe impacts on the individual packaging, because the head is clamped in the clamping holder.

In this way it is ensured, for example when using the individual packaging for packaging of surgical bone nails, that the sharp-edged thread of the bone nail no longer makes contact with the inside of the sleeve part of the packaging, even in the event of severe impacts on the individual packaging, because the head of the bone nail is clamped in the clamping collar.

As a result, the risk that the sharp-edged thread of the bone nail could pick up plastic particles from the inside of the individual packaging has been eliminated.

Also in the case of the individual packaging of precision-machined ejector pins provided with a head, contact of the bolt-side end of the ejector pins with the inside of the packaging is prevented.

The one-piece embodiment of the individual packaging is an advantage of the invention; this results in simple and price-advantageous production. Also, an additional closure cap can be provided for closing off the container, which cap is set on or screwed on.

The object of the present invention is evident not only from the object of the individual claims, but rather also from the combination of the individual claims with one another.

In the following, the invention will be explained in greater detail using a drawings that merely represents one embodiment path. In this regard, further characteristics essential to the invention and advantages of the invention will be evident from the drawing and its description.

BRIEF DESCRIPTION OF THE DRAWINGS

The figures show:

FIG. 1: schematically, a side view of an individual packaging in the clamped position;

FIG. 2: a top view of the individual packaging according to FIG. 1;

FIG. 3: the individual packaging according to FIG. 1 in the open position;

FIG. 4: a top view of the individual packaging according to FIG. 3;

FIG. 5: an enlarged detail view of the clamping holder of a first head shape;

FIG. 6: an enlarged detail view of the clamping holder of a second head shape;

FIG. 7: an enlarged detail view of the clamping holder of a third head shape;

FIG. 8: an enlarged detail view of the clamping holder of a fourth head shape;

DESCRIPTION OF A PRESENTLY PREFERRED EMBODIMENT

Figure 9:
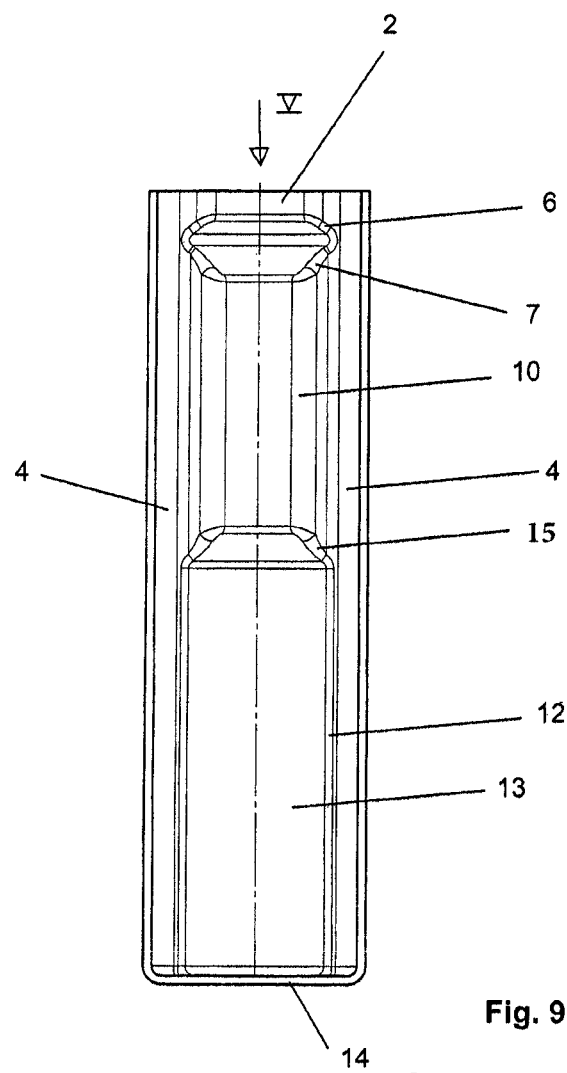
FIG. 9: schematically, in a side view, a section through the individual packaging in the clamped position according to FIG. 1.

The individual packaging 1 consists of an elongated plastic sleeve that is preferably configured to be cylindrical in its basic shape. The invention is not restricted to this. A plastic sleeve having any desired profile shape can be used, such as, for example, also a polygonal plastic sleeve that has a polygon-like cross-section, an oval plastic sleeve, a square or rectangular plastic sleeve or the like. The invention relates to individual packaging for elongate objects such as a screw (20, 30) that consist of at least a head (21) of enlarged diameter and a bolt part (23, 24) adjoining the head and having reduced diameter, such as bone pins, ejector pins, and the like, wherein the individual packaging (1) consists of an approximately cylindrical packaging sleeve, which is open at an end face at least at one end and is made of an elastically bendable material, said packaging sleeve having at least one upper insertion opening (2) for inserting the elongate object (20, 30), wherein the individual packaging (1) holds in a positionally secured manner only the head (21) of the screw (20) to be held in an elastically expandable clamping collar (5) adjacent to the insertion opening (2); in an axial direction and the bolt-side end of the object is held at a distance from the inside of the plastic packaging in such a way that distance is maintained.

Likewise, the invention is not restricted to the type and selection of the elastically deformable material. It is true that an elastically deformable plastic is preferred. However, instead of an elastically deformable plastic, other elastically deformable materials can also be used, such as, for example, paper bodies or paperboard bodies or sleeves that consist of plastic composite materials.

For simplification reasons, the following description is aimed at an individual packaging that is approximately cylindrical in terms of its layout, although the invention is not restricted to this.

An introduction opening 2 is configured at the introduction side of the individual packaging 1, which opening consists of a circumferential ring collar that has a smaller diameter than, for comparison, the clamping collar 5 that follows it directly in the axial direction. The clamping collar 5 is formed by a conically widened inlet collar 6, which follows the upper ring collar 3, and a holding collar 7 that follows the inlet collar 6 and narrows conically in the axial direction.

The elastically expandable clamping collar 5 is accordingly formed, on its underside, by a holding collar 7 that narrows in the axial direction, lies against the underside of the head 21, and makes a transition, upward in the axial direction, into an inlet collar 6 that widens in the axial direction and is provided to lie against the top of the head 21.

It is now important that lateral widened regions 4, approximately in ear shape, follow in the region of the clamping collar 5; in the exemplary embodiment shown, these are disposed to lie diametrically opposite one another, approximately in the same horizontal plane. The two ear-like widened regions accordingly continue the ring collar 3 in the horizontal plane and form regions that lie on the outside, which can be deformed by finger pressure or mechanically. This will be explained later, using FIGS. 3 and 4.

Downward in the axial direction, a first sleeve part 10, which has a first, smaller diameter, follows the clamping collar 5. An elongated object held in the clamped position in the individual packaging 1, for example the screw 20 shown there, therefore has a first, radial free space 11 in the sleeve part 10 with its bolt 23.

The first sleeve part 10 makes a transition into a second sleeve part 12, having a greater diameter, by way of a transition part 15. The sharp-edged threaded part 24 of the bolt 23 of the screw 20 therefore has a greater radial free space 13 relative to the inside of the second sleeve part 12.

Accordingly, the elastically expandable clamping collar 5 is followed, in the axial direction, by the first sleeve part 10 having a first diameter, which makes a transition, by way of a transition part 15, into a second sleeve part 12 having a greater diameter, into which the bolt part and/or the threaded part 23, 24 of the elongated object such as screw 20, 30 project, at least in part, and is secured to prevent it from making contact with the side walls at least of the one sleeve part 12, by means of holding of the head 21 in the clamping collar.

Since the head 21 of the screw 20 is accommodated with force fit in the clamping collar 5, by being clamped, the risk no longer exists that the sharp-edged threaded part 24 makes contact with the inside of the sleeve part 12, even in the event of impacts on the individual packaging. The clamping hold in the clamping collar 5 can actually be configured to be so strong (load-absorbing) that contact of the bolt 23 against an inside of the sleeve part 10 is also prevented.

The clamping hold of the head 21 of the screw takes place in that the underside 23 of the head 21 lies against the inside of the holding collar 7, in clamping manner, and, at the same time, the upper part of the head 21 is held against the inside of the inlet collar 6, in clamping manner. The respective head 21, 21a, 21b, 21c is therefore held at both the top and the underside, with force fit, against the collars 6, 7 of the clamping collar 5, which are inclined in opposite directions.

FIGS. 3 and 4 now show the release position of the individual packaging 1. The same parts are indicated in the release position with a vertical bar or "pipe." It is shown that the two widened regions 4 that lie diametrically opposite one another are compressed in the direction of the arrow 8 with finger pressure or mechanically.

In this way, the ring collar 3 widens radially and assumes its position 3'. At the same time, the sides of the holding collar 7 that lie opposite one another move away from the underside 23 of the head 21 of the screw 20, so that the latter can be taken out of the packaging in the direction of the arrow 16 or automatically falls out of the packaging when the latter is rotated by 180°.

FIG. 3 also shows the widening of the clamping collar 5 in the direction of the arrows 9, directed radially outward.

In the figures, it is also shown that the individual packaging 1 can have a bottom 14. The invention is not restricted to this. The bottom 14 can also be eliminated.

It is furthermore shown that the tip 25 of the object (here, of the screw 20) has a distance from the bottom 14. The invention is also not restricted to this. In another embodiment, it can be provided that the tip 25 of the screw 20 is held in a secure position in a bottom-side or wall-side centering of the individual packaging.

FIGS. 5-8 show different head shapes of elongated objects, all of which are held in a secure position with the clamping collar 5 according to the invention, in the region of the introduction opening 2 of the individual packaging 1.

In FIG. 5, a head 21 of an elongated object having a rounded-off underside 22 is shown.

In FIG. 6, a different head shape of a head 21a is shown. The clamping collar 5 thereby lies against the top and underside of the head 21a with force fit, in a different way.

FIG. 7 shows an approximately cylindrical head 22b, as it is used for the ejector pins 30 of plastic injection-molding molds. The lower edge 26, which is configured to be straight, lies against the inside of the holding collar 7 only at the edge.

FIG. 8 shows an approximately lens-shaped head 21c.

Figure 10:
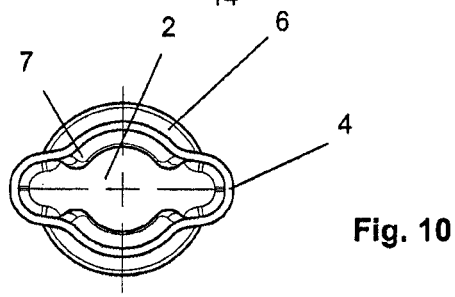
FIG. 10: a top view of FIG. 9 in the direction of the arrow X.

FIG. 9 shows a section through the individual packaging 1 according to FIG. 1, where it can be seen that the radial widened regions 4 extend over the entire length of the individual packaging 1. It has already been pointed out in the general description part of the invention that the invention is not restricted to this. FIG. 10 shows a top view of the arrangement according to FIG. 9, which approximately corresponds to the representation in FIG. 2.

Figures 11, 12:
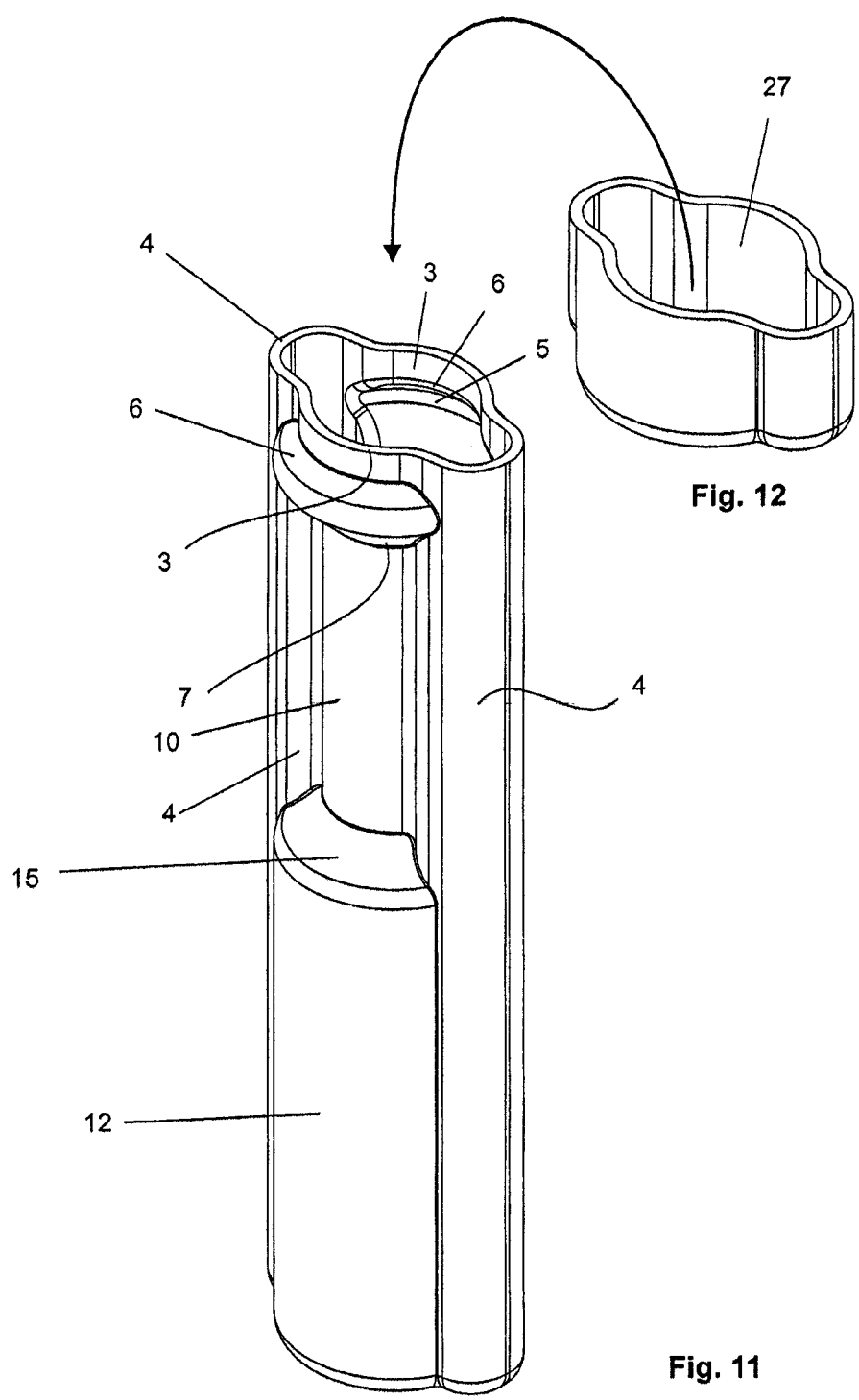
FIG. 11: a perspective side view of the individual packaging.
FIG. 12: a perspective view of the lid.

According to FIG. 11, the two sleeve parts 10, 12 have an approximately cylindrical cross-section and continue outward in the radial direction by means of the widened region 4 on both sides.

FIG. 12 shows a lid 27 that preferably has the same shape as the ring collar 3 and can be set onto the latter. The lid 27 thereby closes off the packaging sleeve, which is open on at least one face side, in the set-on state.

DRAWING KEY

1. Individual packaging
2. Introduction opening
3. Ring collar
4. Widened region
5. Clamping collar
6. Inlet collar
7. Holding collar
8. Arrow direction
9. Arrow direction
10. Sleeve part
11. Free space (of 10)
12. Sleeve part
13. Free space
14. Bottom
15. Transition part
16. Arrow direction
17. -
18. -
19. -
20. Screw
21. Head
22. Underside
23. Bolt
24. Threaded part
25. Tip
26. Lower edge
27. Lid
28. -
29. -
30. Ejector pin

What is claimed is:

1. A packaging for an elongated objects that includes a head having an increased diameter such that said head defines an underside and a top, said elongated object also having a bolt part that adjoins said head and that has a reduced diameter said packaging comprising:
    an approximately cylindrical packaging sleeve that defines an inside surface and an open end, said packaging sleeve being composed of an elastically bendable material and having an opening for introducing the elongated object; and
    an elastically expandable clamping collar that adjoins the opening of said packaging sleeve in the axial direction, said elastically expandable clamping collar having an underside that forms a holding collar that narrows in the axial direction and that contacts the underside of the head, said elastically expandable clamping collar transitioning, in the axial direction, into an inlet collar that widens in the axial direction and that contacts the top of the head of said elongated object to hold the head of the elongated object in a secure position and maintain the bolt part of the elongated object at a distance from the inside of said packaging.

2. The packaging according to claim 1; wherein a sleeve part adjoins said elastically expandable clamping collar in the axial direction, said sleeve part forming a radial free space relative to the bolt part of the elongated object.

3. The packaging according to claim 1 wherein said elastically expandable clamping collar contacts the head of the elongated object only by a circumference region of less than 340 degrees, said elastically expandable clamping collar having diametrically opposite widened regions that laterally follow said inlet collar and said holding collar, said widened regions being elastically deformable and expandable in response to finger pressure.

4. The packaging according to claim 3 wherein said elastically expandable clamping collar has an outer circumference and wherein said diametrically opposite widened regions are located on the outer circumference of said elastically expandable clamping collar and have a greater radius of curvature than said inlet collar and said holding collar that follow radially.

5. The packaging according to claim 3 that includes a total of two diametrically opposite widened regions that are configured to be deformed in the radial direction.

6. The packaging according to claim 3 that includes more than two diametrically opposite widened regions that are configured to be deformed in the radial direction.

7. The packaging according to claim 3 wherein the axial length of said widened regions corresponds to the length of said packaging.

8. The packaging according to claim 3 wherein the axial length of said widened regions is shorter than the length of said packaging.

9. The packaging according to claim 1 wherein a first sleeve part has a first diameter and adjoins said elastically expandable clamping collar in the axial direction, said first sleeve part making a transition into a second sleeve part that has an increased diameter by way of a transition part, the bolt part or threaded part of said elongated object projecting, at least in part into said second sleeve part and said elastically expandable clamping collar securing the head of said elongated object to prevent said elongated object from contacting the side walls of said second sleeve part.

* * * * *

UNITED STATES PATENT AND TRADEMARK OFFICE
CERTIFICATE OF CORRECTION

PATENT NO. : 9,694,968 B2  
APPLICATION NO. : 15/036908  
DATED : July 4, 2017  
INVENTOR(S) : Peter Roesler Page 1 of 1

It is certified that error appears in the above-identified patent and that said Letters Patent is hereby corrected as shown below:

On the Title Page

Please correct item (73):
Assignee: "Rose Plastic AG" to "Roesler IP GMBH"

Signed and Sealed this
Twenty-seventh Day of October, 2020

Andrei Iancu
*Director of the United States Patent and Trademark Office*